United States Patent [19]
Barthelemy et al.

[11] Patent Number: 5,413,100
[45] Date of Patent: May 9, 1995

[54] NON-INVASIVE METHOD FOR THE IN VIVO DETERMINATION OF THE OXYGEN SATURATION RATE OF ARTERIAL BLOOD, AND DEVICE FOR CARRYING OUT THE METHOD

[76] Inventors: Jean-Claude Barthelemy, 12 rue Barra, 42000 Saint-Etienne; André Geyssant, 24 rue Paillard, 42100 Saint-Etienne, both of France

[21] Appl. No.: 184,031

[22] Filed: Jan. 21, 1994

Related U.S. Application Data

[63] Continuation-in-part of Ser. No. 914,322, Jul. 17, 1992, abandoned.

[30] Foreign Application Priority Data

Jul. 17, 1991 [FR] France ................... 91 09020

[51] Int. Cl.⁶ .................................. A61B 5/00
[52] U.S. Cl. ....................... 128/633; 128/664; 128/665; 128/666
[58] Field of Search ................... 128/633–634, 128/664–667; 356/39–41

[56] References Cited

U.S. PATENT DOCUMENTS 4,562,843  1/1986  Djordjevich et al. .
4,846,189  7/1989  Sun .
5,111,817  5/1992  Clark et al. .
5,152,296 10/1992  Simons .

OTHER PUBLICATIONS

"Identification of Vascular Viscoelastic Property Using Adaptive Filter Technique" Nishimura et al., 29th Conference of Japan Society of Medical Electronics & Biological Engineering, May 10th, 1990.

A. Kawarada et al., "Noninvasive Automatic Measurement of Arterial Elasticity in Human Finger and Rabbit Forelegs Using Photoelectric Plethysmography", Medical & Biological Engineering & Computing, vol. 24, No. 6, Nov. 1986, pp. 591-596.

H. Shimazu et al., "Noninvasive Measurement of Frequency Characteristics of Arterial Elastic Modulus in Human Fingers", Proceedings of 26th Conference of Japan Society of Medical Electronics & Biological Engineering Apr. 1-3, 1987, p. 213.

*Primary Examiner*—Angela D. Sykes
*Attorney, Agent, or Firm*—Young & Thompson

[57] ABSTRACT

The apparatus comprises three laser diodes emitting at 660, 750 and 940 nm respectively, excited cyclically at the rate of a timer. The light emitted is channelled by three optical fibers to traverse a fully-vascularized tissue region of a subject along three virtually merged optical paths, and to terminate at an opto-electronic sensor, which generates overlapping signals representative of the molecular absorption. The pulsation of the arterial blood in the region induces variable components which are exclusively a function of the molecular absorptions due to oxyhemoglobin, deoxyhemoglobin and carboxyhemoglobin. The signals are switched by gates on three channels where the variable components are picked up and digitized, and then processed in a microprocessor to yield the oxygen saturation $SaO_2$ and the carbon monoxide fixation of the hemoglobin.

19 Claims, 1 Drawing Sheet

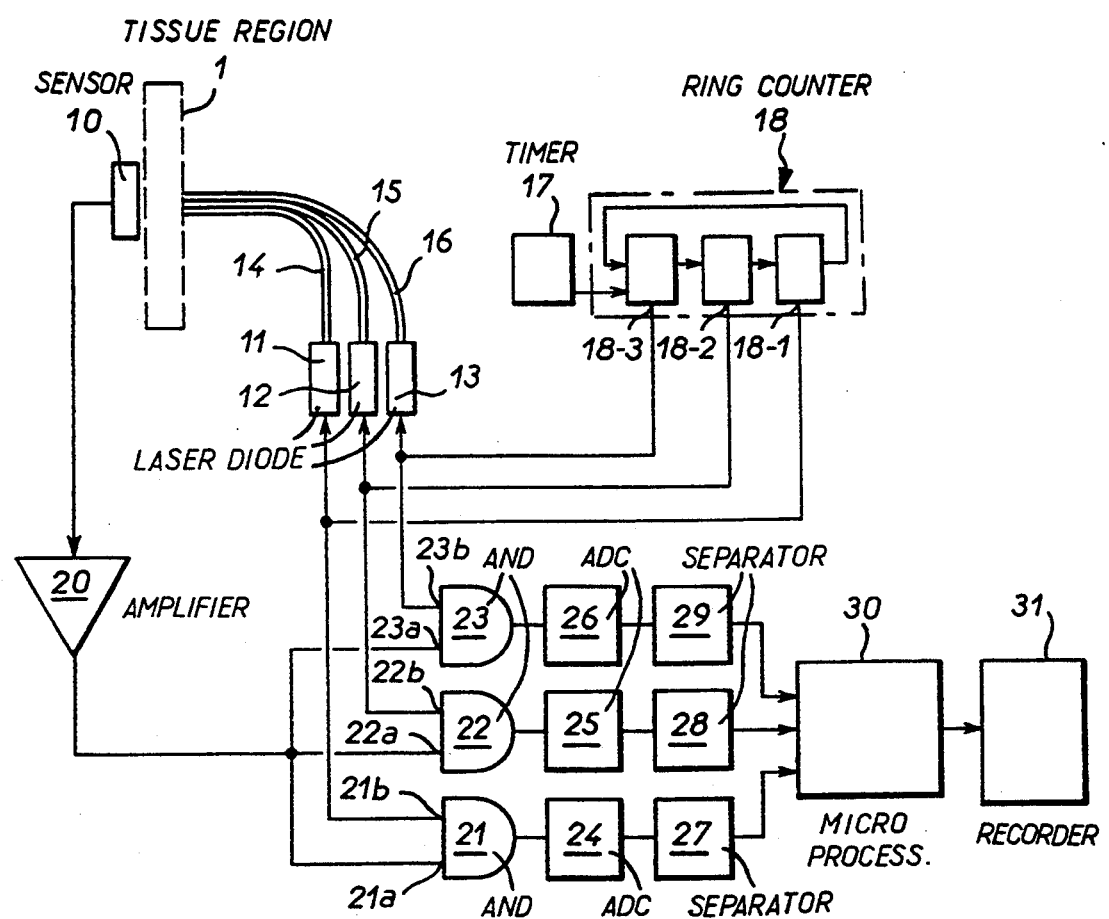

NON-INVASIVE METHOD FOR THE IN VIVO DETERMINATION OF THE OXYGEN SATURATION RATE OF ARTERIAL BLOOD, AND DEVICE FOR CARRYING OUT THE METHOD

This application is a continuation-in-part of U.S. application Ser. No. 07/914,322, filed Jul. 17, 1992, now abandoned.

BACKGROUND OF THE INVENTION

Field of the Invention

The invention concerns a process for determining the oxygen saturation rate of the arterial blood of a subject, by comparison of the concentration of oxyhemoglobin, or $HbO_2$, with the total hemoglobin concentration, in which an opto-electronic sensor is used to acquire representative signals of optical absorption on two paths, crossing an appropriate tissue region of the subject, and emanating from two respective light sources, each emitting in a different wavelength band, one in the near infrared and the second in the deep red, so that these representative signals comprise a variable component corresponding to the absorption by the pulsatile arterial blood, and a continuous component corresponding to the absorption by the other tissues crossed, the variable component of each representative signal being separated, and, using known formulas, the respective rates of $HbO_2$ and deoxyhemoglobin or $Hb$ are calculated from the variable components, and, also using a known method, the oxygen saturation rate is determined therefrom.

The invention also concerns a device for carrying out the method of the invention.

The determination of oxygen saturation rate of the arterial blood helps to determine the capacity of the organism of a subject to respond to the oxygen requirements of the different organs, and, consequently, to appreciate the limits of physical activity that are tolerable without danger, or the need for oxygen therapy.

In a conventional manner, the oxygen saturation rate of the arterial blood, or $SaO_2$, is determined by sampling the arterial blood, and analyzing this blood. These determinations are made at a given time, and do not provide information about variations in time in response to organic requirements.

Between the years 1930 and 1950, oxymeters were designed in particular to monitor the severe hypoxias to which pilots were subjected (Nicolai 1932, Matthes 1935, Squire 1940, Millikan 1942, Wood and Geraci 1949), the procedure involving a measurement of the optical absorption by the tissues, in order to determine a total absorption of the tissues which are drained of blood by compression using a balloon.

Aoyagi (1974) developed a method for the continuous measurement of the arterial saturation, called pulse oxymetry. This method is based on the following considerations.

The soft tissues are relatively transparent in the deep red and the near infrared.

By contrast, hemoglobin, in its different forms including oxyhemoglobin, and deoxyhemoglobin, exhibit pronounced absorptions in these parts of the spectrum.

Oxyhemoglobin displays an absorption curve as a function of wavelength which, in comparison with the absorption curve of deoxyhemoglobin, is lower in the deep red, and higher in the near infrared, so that, by using two measurements at different wavelengths, one in the near infrared and the second in the deep red, knowing the specific absorption coefficients of the two forms of hemoglobin, one can accordingly calculate the relative contents of these two forms, in so far as the only absorptions involved are produced by the forms of hemoglobin.

In the arterial network, the blood flow is pulled to the heart beat. In a tissue region crossed by the optical path between a light source and an opto-electronic sensor, the volume of arterial blood varies with the pulse rate, and hence the absorption of the arterial blood. By contrast, absorption by the tissues in the above tissue region, other than the arterial blood, does not vary, whether for the immobile soft tissues, or the venous blood at constant flow. In consequence, the signal from the opto-electronic sensor comprises a continuous component, corresponding to the absorption by the tissues other than the arterial blood, and a variable component at the rate of the blood pulse rate, which depends only on the blood absorption.

Strictly speaking, another component of the blood exists, which exhibits pronounced absorptions in the region ranging from the near infrared to the deep red, namely cytochrome C oxidase. However, this component also displays a variable absorption with the oxygen concentration in the blood, and in low concentrations compared with the hemoglobin content, so that, if corrections are not introduced to take account of the specific absorption of cytochrome C oxidase, errors in the oxygen saturation remain of the second order.

The Aoyagi method was improved by Nakajima et al (1975), by Yoshiya et al (1980), and Shimada et al (1984), in particular thanks to advances in opto-electronics, and in signal processing electronics.

J. P. Payne and J. W. Severinghaus (1985) published investigations on the absorption curves of the forms of hemoglobin, which recommend the use of two wavelengths, namely 940 nm in the near infrared, and 660 nm in the deep red.

To calculate the oxygen saturation, which is denoted $SaO_2$, the following considerations are applied.

The absorption, expressed by the optical density DO, is governed by the Beer-Lambert Law:

$$DO = e \cdot c \cdot l \qquad (1)$$

where e is the molecular extinction coefficient, c is the concentration of the absorbent component, and l is the length of the optical path in the absorbent medium.

In fact, the total optical density is the sum of the optical densities due to the specific absorptions of the different absorbents.

By proceeding at two different wavelengths, a first degree system of equations with two unknowns is obtained, the unknowns being the oxyhemoglobin and deoxyhemoglobin concentrations, or $HbO_2$ and $Hb$ respectively:

$$\left. \begin{array}{l} DO_{660\,nm} = [e_1(Hb) + e_2(HbO_2)]l \\ DO_{940\,nm} = [e_3(Hb) + e_4(HbO_2)]l \end{array} \right\} \qquad (2)$$

where $e_1$ and $e_3$ are the molecular absorption coefficients of deoxyhemoglobin, and $e_2$ and $e_4$ those of oxyhemoglobin, at 660 and 940 nm respectively.

The resolution of the system (2) is standard, and gives Hb and HbO$_2$, to within a factor of l. Obviously, the paths in the tissues are equal for both of the wavelengths, which presume that these paths are very near to each other.

The oxygen saturation SaO$_2$ is accordingly given by:

$$SaO_2 = HbO_2/(Hb + HbO_2) \tag{3}$$

where the factor l disappears.

It should be clear that the values of DO considered above correspond to the variable component of the signal indicating absorption, owing to the linear character of the combination of the optical densities.

So far, pulse oxymeters were relatively heavy and bulky instruments, only employed in hospital facilities, where it was impossible to take measurements of the oxygen saturation of the arterial blood continuously in conditions similar to those imposed by everyday life. Thus invaluable information could not be obtained on the risks of hypoxia from the standpoints of diagnosis, treatment and lifestyle.

Furthermore, the oxymetries only gave measurements of Hb and HbO$_2$, ignoring a third form of hemoglobin, carboxyhemoglobin, which results from the fixation of carbon monoxide on hemoglobin, with a relatively high bonding energy.

For a long time, certainly, apart from cases of serious carbon monoxide poisoning, the error introduced by the presence of carboxyhemoglobin, or HbCO, in the measurement of oxygen saturation, was ignored. With the spreading battle against smoking and air pollution by automotive vehicles, however, the possibility of determining the HbCO content emerged as increasingly desirable.

The objective of the Applicants was to make an instrument capable of determining the respective shares of Hb, HbO$_2$ and HbCO in the arterial blood, which is readily portable, to be able to determine these Hb, HbO$_2$ and HbCO concentrations on a subject, over a prolonged period, for example a period of 24 h, with the subject exerting activity close to normal.

SUMMARY OF THE INVENTION

To achieve this, the invention proposes a method for determining the oxygen saturation rate of the arterial blood of a subject, in which the concentration of oxyhemoglobin or HbO$_2$ is compared with the total concentration of hemoglobin, comprising the steps of providing first, second and third light sources emitting in respective wavelength bands including a near infrared wavelength band, a deep red wavelength band and a wavelength band therebetween, selectively directing light emitted from the respective light sources through an appropriate tissue region of the subject, acquiring representative signals of optical absorption through the tissue region, cyclicly exciting the light sources in succession and determining the frequency of the cyclic succession so as to be large as compared with the arterial pulsation frequency of the subject, and calculating concentrations of HbO$_2$, Hb and HbCO to determine the oxygen saturation rate.

According to another aspect of the invention, there is provided a method for determining the oxygen saturation rate of the arterial blood of a subject, by comparison of the concentration of oxyhemoglobin, or HbO$_2$, with the concentration of total hemoglobin, including providing two light sources each emitting in a different wavelength band, one in the near infrared and the second in the deep red, directing light emitted by the light sources along two paths through an appropriate tissue region of the subject, providing an opto-electronic sensor for acquiring representative signals of the optical absorption of the light, the representative signals comprising a variable component corresponding to the absorption by the pulsatile arterial blood, and a continuous component corresponding to absorption by the other tissues traversed, separating the variable component of each representative signal, calculating the respective concentrations of HbO$_2$ and deoxyhemoglobin, and optionally Hb, from the variable components, determining the oxygen saturation rate, wherein the improvement comprises the steps of providing a third light source emitting a third wavelength band between the aforesaid two bands and a corresponding third optical path associated with said third light source, exciting the three light sources in cyclic succession, selecting the cyclic succession frequency so as to be large in comparison with the arterial pulsation frequency of the subject, whereby the representative signals overlap, and each representative signal is switched at the cyclic succession rate to a respective separate channel, and calculating HbO$_2$, Hb and HbCO to determine the oxygen saturation rate therefrom.

It goes without saying that the optical paths, as usual, will be taken on relatively small thicknesses of fully-vascularized tissues, such as the ear, or on the fingers.

Operation with three wavelengths, $\lambda_1$, $\lambda_2$ and $\lambda_3$, yields a system of linear equations with three unknowns:

$$\begin{aligned} DO\lambda_1 &= [e_1(Hb) + e_2(HbO_2) + e_5(HbCO)]l \\ DO\lambda_3 &= [e_3(Hb) + e_4(HbO_2) + e_6(HbCO)]l \\ DO\lambda_2 &= [e_7(Hb) + e_8(HbO_2) + e_9(HbCO)]l \end{aligned} \tag{4}$$

which can be resolved by known formulas.

In a similar manner to formula (3), the oxygen saturation of functional hemoglobin, or SbO$_2$, is given by:

$$SbO_2 = HbO_2/(Hb + HbO_2) \tag{5}$$

The oxygen saturation of total hemoglobin, or SaO$_2$, is given by:

$$SaO_2 = HbO_2/(Hb + HbO_2 + HbCO) \tag{6}$$

and the relative content of carboxyhemoglobin in total hemoglobin, or FCO, is given by:

$$FCO = HbCO/(Hb + HbO_2 + HbCO) \tag{7}$$

Furthermore, the use of a single sensor favors the concentration of the optical paths in order to operate on tissues that are as identical as possible, by reducing the inhomogeneities of the tissues crossed, and the differences in length. The cyclic excitation of the three light sources in a pulse régime, at a high frequency compared with the arterial pulsation frequency, after switching to the respective channels, reconstructs the pulsation-dependent curves, from which the variable components can be separated.

Preferentially, the wavelength bands are centered on 940, 660 and 750 nm respectively.

By adopting an intermediate wavelength for the third optical path, a satisfactory separating power is obtained, thanks to the differences between the specific absorptions for the three hemoglobin species, and no absorption discontinuities are introduced for the non-blood tissues.

Preferably, the processing of the representative absorption signals, including the extraction of the variable components and the subsequent calculations, are carried out in a microprocessor under the control of a suitable software.

From another standpoint, the invention proposes an apparatus for determining the oxygen saturation rate of the arterial blood of a subject, in which the concentration of oxyhemoglobin or $HbO_2$ is compared with the total concentration of hemoglobin, comprising first, second and third light sources emitting in respective wavelength bands including a near infrared wavelength band, a deep red wavelength band and a wavelength band therebetween, the respective light sources being directed at an appropriate tissue region of the subject, an opto-electronic sensing means acquiring representative signals of optical absorption through the tissue region, means for cyclicly exciting the light sources in succession, the frequency of the cyclic succession being large as compared with the arterial pulsation frequency of the subject, and means for calculating $HbO_2$, Hb and HbCO to determine the oxygen saturation rate.

According to another aspect of the invention, there is provided an apparatus for determining the oxygen saturation rate of the arterial blood of a subject, comprising light sources emitting in respective wavelength bands, one of the wavelength bands being near infrared and another of the wavelength bands being deep red, opto-electronic sensing means for emitting respective signals responsive to optical absorption along respective optical paths through an appropriate tissue region of the subject, said signals including a variable component corresponding to absorptions by pulsatile arterial blood and a continuous component corresponding to absorption through other tissues traversed, means for separating the variable component of the respective absorption signals, calculating means for processing the variable components and determining the respective concentrations of oxyhemoglobin or $HbO_2$ and deoxyhemoglobin, or Hb, and also determining the oxygen saturation rate, further comprising a third light source emitting a wavelength band intermediate the first two wavelength bands, a third optical path between the third light source and the tissue region, the three optical paths terminating in said optoelectronic sensing means, means for exciting the three light sources in cyclic succession at a cyclic succession frequency which is large in comparison with pulse frequency of the subject whereby the representative of signals overlap, means for switching each of the representative signals to a respective channel at the frequency cyclic succession, said last switching means comprising means for separating the variable component of the representative signal, said calculating means jointly processing the three variable components to identify $HbO_2$, Hb and HbCO and determining the oxygen saturation rate therefrom.

The device is defined in terms of structural elements capable of performing the functions necessary for the operations of which the sequence defines the method of the invention.

Preferably, the light sources consist of laser diodes, approximately monochromatic and capable of high peak light flux.

Moreover, the means for defining the optical paths between the light sources and the tissues are advantageously made of optical fibers, connected in a bundle at their end close to the tissue region traversed. Thus, the optical paths between the optical fibers and the sensor are approximately parallel and adjacent, and practically cross the same tissues across the same length.

At the output of a microprocessor suitably programmed to execute the necessary calculations, but conventional in itself once the formulas are correctly set up, a means of recording is advantageously provided, which periodically records the microprocessor data, in order, by a subsequent reading, to reconstruct the variations in oxygen saturation, as a function of the conditions to which the subject has been subjected.

The device is preferably arranged in a portable unit with self-contained operation of at least a few hours, and preferably at least 24 h. It is hardly necessary to stress the importance of being able to cover a complete Circadian cycle, beginning and ending at the same convenient hour.

BRIEF DESCRIPTION OF THE DRAWING

Secondary characteristics and advantages of the invention also emerged from the description that follows, provided as an example, by reference to the appended drawing in which the single figure is a schematic of a device according to the invention.

DETAILED DESCRIPTION OF THE INVENTION

According to the embodiment selected and shown in this figure, three light emitters are placed on either side of a fully-vascularized tissue region 1 of an experimental subject, for example an external ear, the three light emitters each consisting of an laser diode 11, 12, 13 and a optical fiber 14, 15, 16 respectively, the optical fibers being connected and bound together in a bundle perpendicular to the tissue region 1, and an opto-electronic sensor 10. The laser diodes are capable of emitting on respective wavelengths of 660, 750 and 940 nm respectively, to within a few nanometers. The optical paths across the tissue region 1 from the end section of the optical fibers 14, 15, 16 to the sensor are hence virtually merged and perpendicular to the general plane of the tissue region 1.

The opto-electronic sensor is selected to have a uniform sensitivity between 660 and 940 nm, or at least a monotonic variation in sensitivity, and especially without resonance or cutoff bands. The opto-electronic sensor is followed by an amplifier 20, such that the useful signal level at the amplifier output is suitable.

A timer 17 drives a counter by three, mounted in a ring, of which the outputs 18-1, 18-2 and 18-3 drive the laser diodes 11, 12 and 13 respectively, so that the diodes, each in its turn, emit a light pulse, on their respective wavelengths.

The operating frequency of the timer 17, three times the frequency of one cycle of the ring counter 18, is selected to be large in comparison with the pulsation frequency of the subject, which generally ranges between 1 and 2 Hz, so that the variable components of absorption, at the pulsation frequency of the arterial blood, are suitably reproduced. In practice, one cycle of the ring counter lasts about 40 microseconds, and cycles are repeated approximately every 9 milliseconds. Thus, the timer frequency ie about 75 kHz, and the recurrence frequency of the cycles is about 100–120 Hz.

It can be easily understood that the laser diodes 11, 12 and 13 possess their own power supply and pulse triggering circuits, the signals emanating from the ring counter 18 being control signals, and not power signals.

The light pulses supplied by the laser diodes 11, 12 and 13, and guided by the optical fibers 14, 15 and 16, cross the tissue region 1 where they undergo absorptions, and reach the sensor 10, where they cause the formation of electrical signals which are a function of the light energy received, and hence indicative of the molecular absorption that has occurred. These signals are brought to a suitable level by an amplifier 20. The cyclic succession of the emission of the three diedes 11, 12 and 13 results in an interlacing of the signals corresponding to the three wavelengths.

At the output of the amplifier 20, the signals drive a program switch formed of three analogue ET gates 21, 22 and 23. These signals are applied in parallel to the logic inputs 21a, 22a and 23a, while the logic control inputs 21b, 22b and 23b are driven by the signals leaving the outputs 18-1, 18-2 and 18-3 respectively from the ring counter 18.

Three respective channels are positioned at the output of the ET gates 21, 22 and 23, each consisting of an analogue-to-digital converter 24, 25, 26, followed by a variable component separator stage 27, 28, 29.

Since the opening of the gates 21, 22 and 23 is respectively synchronous with the emissions of the light signals by the laser diodes 11, 12 and 13, the channel placed downstream from the gate 21 processes the significant absorption signals at 660 nm, the channel downstream of gate 22 processes those of the absorption at 750 nm, and the channel downstream of gate 23 processes those of the absorption at 940 nm.

The analogue-to-digital converters 24, 28, 26 hence generate numerical signals representative of the absorption at the three wavelengths at the inputs of a microprocessor 30 after inhibition of the continuous component. This first performs the calculations per channel to indicate the representative signals of variable absorption, digitized, in optical density data, taking account of adjustments for the yield of the laser diodes, of specific absorptions of the optical circuits, and of the efficiency of the sensor 10 at the wavelength considered, the adjustment parameters being determined by suitable calibration. The microprocessor then resolves equation (4) for the unknowns Hb, $HbO_2$ and HbCO. Using the values of Hb, $HbO_2$ and HbCO, the microprocessor 30 determines (equations (5) and (6)) the values of $SaO_2$ and FCO.

The values are stored by accumulation. The memories are dumped periodically to determine the average values of $SaO_2$ and FCO over the period elapsed. These values are sent to a recorder 31, for example of the cassette magnetic tape type. The reading of the cassette subsequently serves to retrieve the values of $SaO_2$ and FCO with their variations corresponding to the conditions undergone by the subject during the testing period.

The device is normally made of two components. A probe combines an end mounting for the optical fibers 14, 15 and 16, and the sensor 10, in a structure fixed on either side of the tissue region selected, for example the external ear. The second component comprises the diodes 11, 12 and 13, the different control, switching and computation circuits, with the recorder and a self-contained power supply, of the rechargeable battery type, and is accommodated in a case forming a bag. A cable, containing the connecting conductor to the sensor 10, and the optical fibers 11, 12 and 13, connects the case to the probe. The system looks something like a WALKMAN type cassette player.

Note that it is possible to place only one optical fiber in the cable, positioned at the output of a multiplexer driven by the optical fibers 11, 12 and 13, shortened accordingly, this arrangement also ensuring that the three optical paths are completely merged when crossing the tissues.

It should be pointed out that the integrated design of the specific calculations for $SaO_2$ and FCO, which replaces the use of the absorption bands in a computation system standardized by current methods, allows a miniaturization of the hardware, making it possible to construct a portable self-contained instrument, and, as a corollary, the performance of measurements within the framework of natural physical activities, and over periods ranging up to one Circadian cycle.

Naturally, the invention is not limited to the example described, but embodies all the variants of execution, within the framework of the claims.

In particular, everything connected with the control of the cyclic succession of triggerings by the laser diodes, and with the switching of the representative signals, can be achieved by the microprocessor 30 if suitably programmed. The execution in distinct circuits described above corresponds to a concern to clarify the description.

The text has already mentioned the concentration of the three optical paths of the three wavelengths in a common section comprising the crossing of the tissue zone, the three optical fibers connected to the sources culminating in a multiplexer from which a single fiber departs.

On the other hand, the creation of an adapted software lies beyond the scope of this invention, and is within the domain of specialist programmers who are familiar with the type of the input data, and with the processing that they must undergo to yield appropriate output data.

Finally, it goes without saying that the recorder 31 may be of any suitable type, for example a floppy 'disc' instead of a cassette tape.

What we claim is:

1. Method for determining the oxygen saturation rate of the arterial blood of a subject, in which the concentration of oxyhemoglobin or $HbO_2$ is compared with the total concentration of hemoglobin, comprising the steps of providing first, second and third light sources emitting in respective wavelength bands including a near infrared wavelength band, a deep red wavelength band and a wavelength band therebetween, selectively directing light emitted from the respective light sources through an appropriate tissue region of the subject, acquiring representative signals of optical absorption through the tissue region, cyclicly exciting the light sources in succession and determining the frequency of the cyclic succession so as to be large as compared with the arterial pulsation frequency of the subject, and calculating concentrations of $HbO_2$, Hb and HbCO to determine the oxygen saturation rate.

2. Method according to claim 1, wherein the wavelength bands are centered on 940, 660 and 750 nm respectively.

3. Method for determining the oxygen saturation rate of the arterial blood of a subject, by comparison of the concentration of oxyhemoglobin, or $HbO_2$, with the concentration of total hemoglobin, including providing two light sources each emitting in a different wavelength band, one in near infrared and the second in deep red, directing light emitted by the light sources along two paths through an appropriate tissue region of the subject, providing an opto-electronic sensor for acquiring representative signals of optical absorption of the light, the representative signals comprising a variable component corresponding to absorption by pulsatile arterial blood, and a continuous component corresponding to absorption by the other tissues traversed, separating the variable component of each representative signal, calculating the respective concentrations of oxyhemoglobin, and deoxyhemoglobin or Hb, from the variable components, determining the oxygen saturation rate, wherein the improvement comprises the steps of providing a third light source emitting a third wavelength band between the aforesaid two bands and a corresponding third optical path associated with said third light source, exciting the three light sources in cyclic succession, selecting cyclic succession frequency so as to be large in comparison with the arterial pulsation frequency of the subject, whereby the representative signals overlap, and each representative signal is switched at the cyclic succession rate to a respective separate channel, and calculating concentrations of $HbO_2$, Hb and HbCO to determine the oxygen saturation rate therefrom.

4. Method as claimed in claim 3, characterized in that the wavelength bands are centered on 940, 660 and 750 nm respectively.

5. Method as claimed in claim 3, wherein the representative absorption signals are processed by extracting the variable components and performing the subsequent calculations in a suitably programmed microprocessor.

6. Apparatus for determining the oxygen saturation rate of the arterial blood of a subject, in which the concentration of oxyhemoglobin or $HbO_2$ is compared with the total concentration of hemoglobin, comprising first, second and third light sources emitting light in respective wavelength bands including a near infrared wavelength band, a deep red wavelength band and a wavelength band therebetween, the respective light sources being directed at an appropriate tissue region of the subject, an opto-electronic sensing means acquiring representative signals of optical absorption of the admitted light through the tissue region, means for cyclicly exciting the light sources in succession, frequency of the cyclic succession being large as compared with the arterial pulsation frequency of the subject, and means for calculating concentrations of $HbO_2$, Hb and HbCO to determine oxygen saturation rate.

7. Apparatus according to claim 6, wherein each of said light sources comprises a laser diode.

8. Apparatus according to claim 6, further comprising means for defining optical paths including optical fibers between the respective light sources and the tissue region bundled at an end of the optical fibers adjacent the tissue region.

9. Apparatus according to claim 8, wherein said power supply is capable of supplying power for about 24 hr.

10. Apparatus according to claim 6, wherein said means for calculating concentrations of $HbO_2$, Hb and HbCO, comprises a suitably programmed microprocessor.

11. Apparatus according to claim 10, wherein means for recording data produced by said microprocessor are connected to said microprocessor.

12. Apparatus according to claim 11, wherein said apparatus is a self contained portable unit with its own power supply.

13. Apparatus for determining the oxygen saturation rate of the arterial blood of a subject, comprising light sources emitting in respective wavelength bands, one of the wavelength bands being near infrared and another of the wavelength bands being deep red, opto-electronic sensing means for emitting respective signals responsive to optical absorption along respective optical paths through an appropriate tissue region of the subject, said signals including a variable component corresponding to absorptions by pulsatile arterial blood and a continuous component corresponding to absorption through other tissues traversed, means for separating the variable component of the respective absorption signals, calculating means for processing the variable components and determining the respective concentrations of oxyhemoglobin or $HbO_2$, and deoxyhemoglobin or Hb, and also determining the oxygen saturation rate, further comprising a third light source emitting a wavelength band intermediate the first two wavelength bands, a third optical path between the third light source and the tissue region, the three optical paths terminating in said opto-electronic sensing means, means for exciting the three light sources in cyclic succession at a cyclic succession frequency which is large in comparison with pulse frequency of the subject whereby the representative signals overlap, means for switching each of the representative signals to a respective channel at the frequency of cyclic succession, said switching means comprising means for separating the variable component of the representative signal, said calculating means jointly processing the three variable components to identify $HbO_2$, Hb and HbCO and determining the oxygen saturation rate therefrom.

14. Apparatus according to claim 13, wherein each of said light sources comprises a laser diode.

15. Apparatus according to claim 13, further comprising means for defining optical paths including optical fibers between the light sources and the tissue region, the fibers being bundled at an end adjacent the tissue region.

16. Apparatus according to claim 13, wherein said means for calculating concentration of $HbO_2$, Hb and HbCO, comprises a suitably programmed microprocessor.

17. Apparatus according to claim 16, wherein means for recording data produced by said microprocessor are connected to said microprocessor.

18. Apparatus according to claim 17, wherein said apparatus is a self contained portable unit with its own power supply.

19. Apparatus according to claim 18, wherein said power supply is capable of supplying power for about 24 hr.

* * * * *